(12) United States Patent
Gundersen (10) Patent No.: US 9,079,208 B2
(45) Date of Patent: Jul. 14, 2015

(54) HINGED PAD WITH SOFT EDGE

(75) Inventor: Dag H. Gundersen, Tolvsrød (NO)

(73) Assignee: PadTech AS, Oslo (NO)

( * ) Notice: Subject to any disclaimer, the term of this patent is extended or adjusted under 35 U.S.C. 154(b) by 204 days.

(21) Appl. No.: 13/825,334

(22) PCT Filed: Sep. 28, 2011

(86) PCT No.: PCT/EP2011/066836
§ 371 (c)(1),
(2), (4) Date: Jun. 17, 2013

(87) PCT Pub. No.: WO2012/041893
PCT Pub. Date: Apr. 5, 2012

(65) Prior Publication Data
US 2014/0369737 A1     Dec. 18, 2014

(30) Foreign Application Priority Data

Sep. 29, 2010   (NO) .................................... 20101348

(51) Int. Cl.
| | |
|---|---|
| A61K 9/70 | (2006.01) |
| B05C 17/00 | (2006.01) |
| A45D 37/00 | (2006.01) |
| A61F 13/00 | (2006.01) |

(52) U.S. Cl.
CPC ............. *B05C 17/00* (2013.01); *A45D 37/00* (2013.01); *A45D 2200/1018* (2013.01); *A45D 2200/1036* (2013.01); *A61F 13/00085* (2013.01); *A61F 2013/00297* (2013.01); *A61F 2013/00574* (2013.01); *A61F 2013/00795* (2013.01); *A61F 2013/00902* (2013.01); *A61K 9/703* (2013.01)

(58) Field of Classification Search
CPC ................................ B65D 75/366; B32B 7/04
USPC ....................................... 401/132, 133; 604/3
See application file for complete search history.

(56) References Cited

U.S. PATENT DOCUMENTS

| 6,007,264 A | 12/1999 | Koptis |
| 2006/0163101 A1 | 7/2006 | Assie |

FOREIGN PATENT DOCUMENTS

| CN | 2007841750 | 12/2009 |
| EP | 0368408 Y | 5/1990 |

(Continued)

OTHER PUBLICATIONS

Office Action of Apr. 2, 2014 from Chinese Patent Office (and English translation).

(Continued)

*Primary Examiner* — David Walczak
*Assistant Examiner* — Joshua Wiljanen
(74) *Attorney, Agent, or Firm* — Christian D. Abel (57) ABSTRACT

The present invention relates to a laminated pad that is used to apply a fluid, liquid or a colloidal substance in a controlled manner onto a surface, wherein the pad comprises a top and bottom layer between which top and bottom layer at least one layer is arranged, a utility layer being arranged on an outside of the bottom layer, the top layer, at least one layer, bottom layer and utility layer being connected to form a closed storage chamber for a substance that is to be contained in the pad, where at least a part of the top and bottom layer outside and around the closed storage chamber is cut off in order to create a soft edge around the periphery of the pad, where a hinged layer, the at least one layer and the utility layer are connected around their outer edges to form a laminated pad.

9 Claims, 5 Drawing Sheets (56) References Cited

FOREIGN PATENT DOCUMENTS

| | | |
|---|---|---|
| FR | 2848535 Y | 6/2004 |
| WO | 90/07296 Y | 7/1990 |
| WO | 2009/009651 Y | 1/2009 |
| WO | 2010/101474 | 9/2010 |
| WO | 2010/101474 Y | 9/2010 |
| WO | 2005/089611 Y | 3/2011 |

OTHER PUBLICATIONS

CN Office action of Nov. 15, 2014, submitted inter alia as statement of relevance for non-English references.

HINGED PAD WITH SOFT EDGE

The present invention relates to a device for delivering and applying, in a controlled manner, a quantity of a substance on a desired surface, where the structure of the device prevents irritation and/or damage on the desired surface when the device is used. The device of the present invention applies especially to delivery of substances like pharmaceuticals, cosmetics, hygienic substances, perfume or perfumed substances etc., as the device is provided with a soft edge.

In a number of different situations there is a need for a device that is adapted for applying a substance on a desired surface or area. This may for example involve the application of shoe cream, cosmetics, moisturizing creams, cleansing creams, self-tanning creams, various gel products for personal hygiene, for example soaps, detergents or similar substances or the like.

The substance to be applied may for instance be stored in a bottle, from which the user pours or dispenses a suitable amount of the substance on his/her palms and then manually applies the substance on the desired surface. One other method is to have separate bottles and applicator elements. The substance is then applied onto the applicator element, which will soak up a quantity of the substance, whereby the user will use the applicator element to disperse the substance on the desired surface or area.

Yet another method for applying a substance on a desired surface involves using a disposable or single-use applicator which is supplied with a pre-determined quantity of a substance. Such applicators are manufactured from disposable materials substantially fully infused with the appropriate substance and sealed in a chamber within the applicator.

Common for all known above described devices is that they will result in the user soiling or contaminating his/her hands, either by bringing the substance in direct contact with their hands, or by the device leaking.

Many of the known applicators will also have a tendency to leak and/or to desiccate after that the applicator has been stored for a while. Due to this, the applicators are often manufactured from materials that are relatively thick and stiff. However, as these applicator have relatively sharp and stiff edges, this may cause the surface to which the substance is to be applied, to be scraped and/or injured, especially if the surface is sensitive, for instance if the applicator is used to apply the product to human skin.

Furthermore, none of the known devices are able to provide treatment of the surface or area onto which the substance is to be applied, which in many instances may be desirable to prepare the surface to assist in achieving the optimal function of the substance applied.

WO 90/07296 A1 discloses a cleaning mitt provided with a hand compartment proportioned to accommodated a hand of the user. A cleaning pad, which may be permeated with a cleaning solution, is mounted on the front face of the mitt. A cover is also secured to the front face of the mitt covering the cleaning pad. In use the cover is removed from its position covering the pad, thus exposing the pad for use as a cleaning implement. Features such as outer and inner tabs to aid in removal of the cover from the mitt and the mitt from the hand may be provided. Also outer and inner cuffs may form pockets that aid in the convenient and sanitary disposal of the mitt.

Thus, there is a need for a device for delivering and applying, in a controlled manner, a quantity of a substance to a desired surface, where the device will not leak and/or desiccate during the transportation and/or storage of the device, but where the device on the other hand will be soft enough to prevent irritation and/or damage during the application of the substance on said surface.

It is therefore an object of the present invention to provide a disposable pad for containing and dispensing a substance in a convenient, uniform and simple manner to a desired surface or area, while at the same time providing a disposable pad with soft edges, such that irritation and/or damage of the desired surface is avoided during use of the pad.

These objectives are achieved with a disposable laminated pad for applying a substance onto a surface according to the invention as defined in the enclosed independent claim, where embodiments of the invention are given in the dependent claims.

A typical device according to the present invention may for example consist of six different main layers, where a top layer and a pocket layer will form the outer surfaces of the device.

The device according to the present invention concerns a laminated pad for applying a quantity of a substance on a desired surface, in a controlled manner, where the laminated pad comprises an substantially impermeable top layer and a substantially impermeable bottom layer, between which two layers at least one layer is arranged, where the top layer, a utility layer further being arranged on an outside of the bottom layer, where the top layer, the at least one layer, the bottom layer and possibly also the utility layer are connected together to form a closed storage chamber for a substance that is to be contained in the laminated pad. At least a part of the top layer and the bottom layer outside and around the closed chamber is cut off, in order to create a soft edge around the periphery of the laminated pad, where a hinged layer is arranged over the top layer, the hinged layer, the at least one layer and the utility layer further being connected around their outer edges to form a "closed" laminated pad.

The above described laminated pad will form a pad containing the substance within the closed chamber, where the laminated pad will remain sealed until the top layer is removed prior to the use of the laminated pad. Before the laminated pad is to be used, the hinged layer is folded around or turned inside out around its periphery, such that the top layer is exposed. The top layer can then be removed. The hinged layer will then, by being folded around or turned inside out around its periphery, bend the edge of the pad, whereby this will provide a soft edge around the laminated pad.

After removing the top layer, the stored substance may be squeezed through a contact layer, which layer is in contact with the surface onto which the application is intended.

In one embodiment of the present invention the laminated pad comprises a storage layer, where the storage layer is arranged between the bottom layer and the contact layer.

The laminated pad according to the present invention is primarily intended to be utilized as an applicator for the human body, but it may also be used in the house.

In order to simplify the use of the laminated pad, a side of the utility layer that is facing away from the other layers may be provided with a holding device. The holding device is in its simplest form a cover that is attached to the utility layer in order to form an open cavity, into which cavity a hand, finger or a utensil may be inserted into when the laminated pad is used. The cover may for instance be manufactured from a non-elastic, elastic or non-woven material.

The top layer is used even in cases when it is not absolutely necessary to provide a sealed construction. The purpose of the top layer in these cases will then be to protect the underlying layer or layers from contaminating substances and/or outer exposure, whereby the layer may be manufactured from a cheaper material.

The degree of "sealing" will therefore be dependent on the substance that is to be stored within the laminated pad.

Depending on the properties of the fluid, liquid or colloidal substance to be stored within the laminated pad, the laminated pad can be filled with an appropriate amount of the substance either before the joining of the different layers, or after the layers has been joined together. In this case the substance has to be supplied through one or more of the layers, for instance by a needle.

The top layer is joined to the underlying layers for example by welding. As the top layer has to be removed before the laminated pad is used, the top layer is welded in an area closer to the centre of the layer (inner welding) wherein the weld strength is adjusted to ease the removal of the top layer. The welding of the different layers may also be accomplished in order to form separate compartments in the laminated pad, where this for instance may be desirable if the laminated pad contains two or more substances which are not to be in contact with each other before the pad is used. The welding will then separate the different substances, whereby the removal of the top layer will allow the different substances to be mixed and/or to react with each other.

The different layers of the laminated pad may be manufactured from different materials, wherein the materials furthermore may have different thickness, different properties etc. The layers may also differ in size, form and the way in which they are positioned relative to each other.

The welding of the different layers may be carried out by ultrasound, laser, heat welding etc. Furthermore, the welding may be a string or line, or it may be a spot weld.

The cutting may be carried out by knife, laser, ultrasound etc.

Having thus generally described the nature of the present invention, reference will now be made to the accompanying drawings, showing by way of illustration the preferred embodiments thereof, in which.

Figure 1:
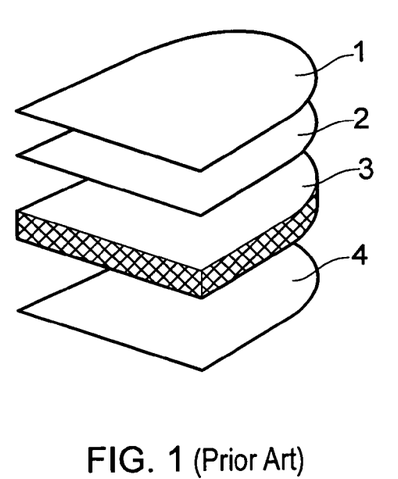
FIG. 1 shows a prior art device in an exploded view, showing the principal configuration of a prior art device.

FIG. 1 shows a principal configuration of a prior art device, where the device is comprised of four different layers 1-4, each of the layers 1-4 having its own specific function. A bottom layer 4 and a top layer 1 will form the outer sealing surfaces of the device. When the different layers of the device are arranged together, the different layers 1-4 are joined around their outer periphery in order to form a sealed construction. This will prevent leakage and/or desiccation of a liquid or a substance contained within the device, for instance a moisturizing cream, during the transportation, storage and/or use of the device.

Between the outer bottom layer 4 and top layer 1 in FIG. 1 a storage layer 3 and a contact layer 2 are arranged. The storage layer 3, which is arranged adjacent the bottom layer 4, contains the liquid or substance that is to be delivered and applied on a desired surface. The liquid or substance that is to be contained within the device can then either be supplied to the storage layer 3 before the different layers 1-4 are connected together or it can be supplied after that the different layers 1-4 have been connected to each other to form the closed device.

The contact layer 2 in FIG. 1 is arranged on the top of the storage layer 3, where the contact layer 2 will allow the substance contained in the storage layer 3 to pass over the contact layer 2 and to the surface on which the product is to be applied. The upper side of the contact layer 2, i.e. a side facing the surface which is to be applied a substance, will then disperse the substance onto the surface in a more even way.

The different layers 1-4 of the device of FIG. 1 will then in appropriate ways be connected to each other, for instance by joining or bonding the layers 1-4 together. However, as the bottom layer 4 and the top layer 1 are manufactured from materials which may be thicker and less flexible than the rest of the layers 2-3, so as to prevent leakage and/or desiccation, the device may have relatively stiff and sharp edges around its periphery, which is not desirable if the device is to be used to apply a product on a part of a human body.

Figure 2:
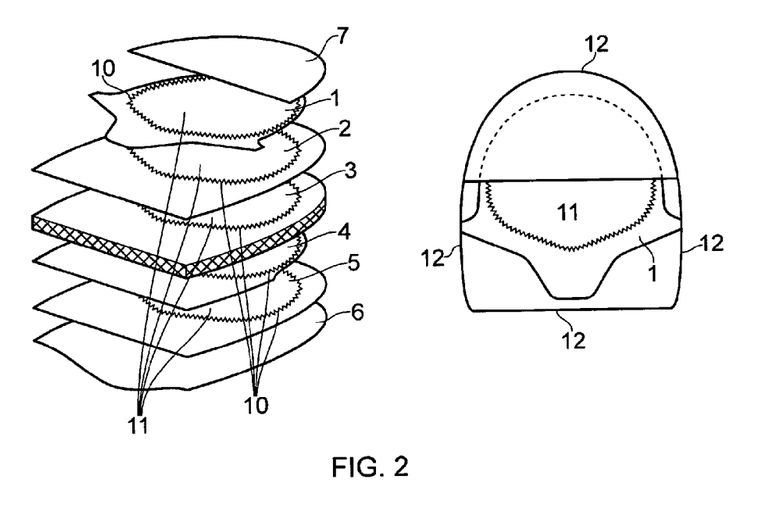
FIG. 2 shows an embodiment of a device according to the present invention, seen in an exploded view and from above.

FIG. 2 shows one embodiment of a device according to the present invention. The device is in form of a disposable handheld laminated pad, where the laminated pad comprises six different individual layers 1-6. Each layer has its own function, but one can also obtain a specific function by combining two or more of the individual layers 1-6.

As the laminated pad according to the present invention contain a liquid or a corresponding substance that may leak or evaporate, the laminated pad is sealed up with a top layer 1 which acts as a protective cover. The top layer 1 is then to be removed by tearing it off before the laminated pad is used, and the top layer is therefore attached by an inner welding 10, to the remaining layers 2-5 of the laminated pad. This inner welding 10 will also form a closed storage chamber 11 for the liquid or a corresponding substance that is contained in the pad. However, it should be understood that the top layer 1 in addition can also be connected to the remaining layers 2-5 at least over a part of its periphery.

The attachment of the different layers 1-5, through the welding 10, can be done in many different ways, for instance welding by ultrasound, heat welding, gluing etc.

In order to ease the removal of the top layer 1, the top layer 1 may be formed with a flap or corner F.

Furthermore, the top layer 1 is manufactured from a substantially liquid-impermeable material.

A bottom layer 4 forms the other outer side of the laminated pad according to the present invention, this meaning that the other layers 2-3 are arranged between the top layer 1 and the bottom layer 5. As the bottom layer 4, like the top layer 1, must prevent the fluid, liquid or colloidal substance passing through it during the transport, storage or use of the laminated pad according to the present invention, the bottom layer 4 is made from a substantially liquid-impermeable material, for instance the same material as the top layer 1.

As the top layer 1 and the bottom layer 4 are substantially liquid-impermeable, the top layer 1 and bottom layer 4 may be manufactured from relatively stiff and "sharp" materials, which can scrape or damage the surface that is to be treated, at least a part of the top and/or bottom layer 1, 4 is cut off or cut out during the manufacturing of the device, where the cut is done outside and around the closed storage chamber 11.

However, if the product to be contained in the device is a thin product or has low viscosity, the product may flow over the closed storage chamber 11 and around the edges of the bottom layer 4, thereby contaminating the user's hands. In order to prevent this, a utility layer 5 is arranged under the bottom layer 4, i.e. on an opposite side of the storage layer 3. The utility layer 5 is manufactured from a material that is substantially liquid-impermeable, but is "thinner" and more flexible than the top layer and the bottom layer.

The utility layer 5 may be provided with a holding device on its side that is turning away from the bottom layer 4. The holding device is a pocket layer 6 that is attached to the bottom layer 4 in order to form an open cavity with the bottom layer 4, into which cavity a hand, finger or utensil may be inserted when the laminated pad according to the present invention is used. The pocket layer 6 is manufactured e.g. from an elastic, non-elastic and/or non-woven material.

A storage layer 3 is arranged above the bottom layer 4. As the storage layer 3 contains the fluid, liquid or colloidal substance that is to be applied onto a surface, the storage layer has a certain thickness. It is manufactured from a non-woven material, for instance a fibre structure, wherein the material has sufficient porosity to store the substance to be applied. Depending on the nature of the substance to be stored within the storage layer 3, the substance can either be supplied to the storage layer before the different layers 1-5 are connected or bonded together, or it can be supplied after the different layers 1-5 have been connected or bonded together.

The pad of the invention may also lack a storage layer 3, and in this particular embodiment the substance to be delivered at a surface may be stored between the bottom layer 4 and the contact layer 2, wherein the top layer 1 ensures that the substance does not escape through the contact layer 2 until removal of the top layer 1.

The contact layer 2 serves as a "passage" layer, as this layer will allow the substance to pass through from the storage layer 3, or from the space between the bottom layer 4 and the contact layer 2, and to the surface on which the substance is to be applied. The contact layer 2 may for example be manufactured from a non-woven material or a plastic material, where the plastic material then is perforated or apertured. According to the present invention, the contact layer 2 is also manufactured in such a way that it provides a brushing or scrubbing effect. This brushing and/or scrubbing effect may then clean or remove dirt from the desired surface, where after the fluid, liquid or colloidal substance is applied onto the surface. This brushing and/or scrubbing effect may also treat the substance to be delivered to obtain a desired effect for the substance, or prepare the surface for application of the substance to be delivered from the pad of the invention.

When the laminated pad shown in FIG. 2 is "finished", the top layer 1, contact layer 2, storage layer 3, bottom layer 4 and utility layer 5 are connected to each other by the weld 10. This weld 10 will also provide a closed storage chamber 11 in the laminated pad, where the closed storage chamber 11 is to contain the fluid, liquid or the colloidal substance. Furthermore, the pocket layer 6, the utility layer 5, the storage layer 3, the contact layer 2 and the hinged layer 7 are connected, for instance by a weld 12, around their outer edges to form a closed laminated pad.

Figure 3:
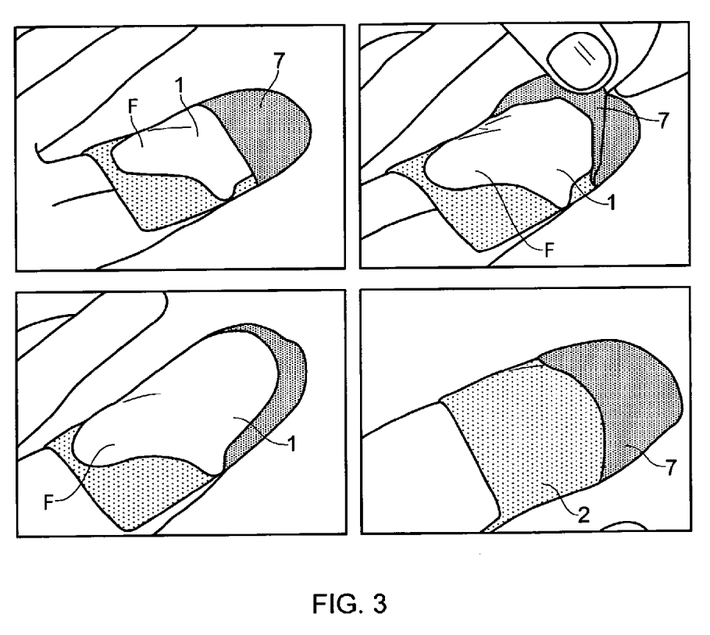
FIG. 3 shows the embodiment of the device illustrated in FIG. 2, where the device is formed to fit onto a user's fingers, where a hinged layer is folded away to reveal a top layer of the device.

FIG. 3 shows a laminated pad according to the present invention, in which the user can insert his/her finger(s), utensil etc. When the laminated pad is to be used (see uppermost left figure), the hinged layer 7 (see uppermost right figure) is folded around or turned inside out around the edge of the laminated pad, whereby the underlying top layer 1 is revealed (see lower left figure). The top layer 1 can then be removed by pulling off the flap F. This will unseal the laminated pad and the contact layer 2 (see lower right figure) is used to apply the product contained in the laminated pad on a desired surface.

When the laminated pad is used, the hinged layer 7 can be folded back to its initial position, thereby partly covering the contact layer 2.

Furthermore, the hinged layer 7 may also be provided with a flap or corner in order to ease the handling of the hinged layer 7

The folding or turning inside out of the hinged layer 7 around the edge of the pad will result in the edge of the pad becoming bent, where this, together with the top and/or bottom layer (which is/are cut off or cut), will provide a pad with a soft edge around at least a part of the periphery of the laminated pad.

Figure 4:
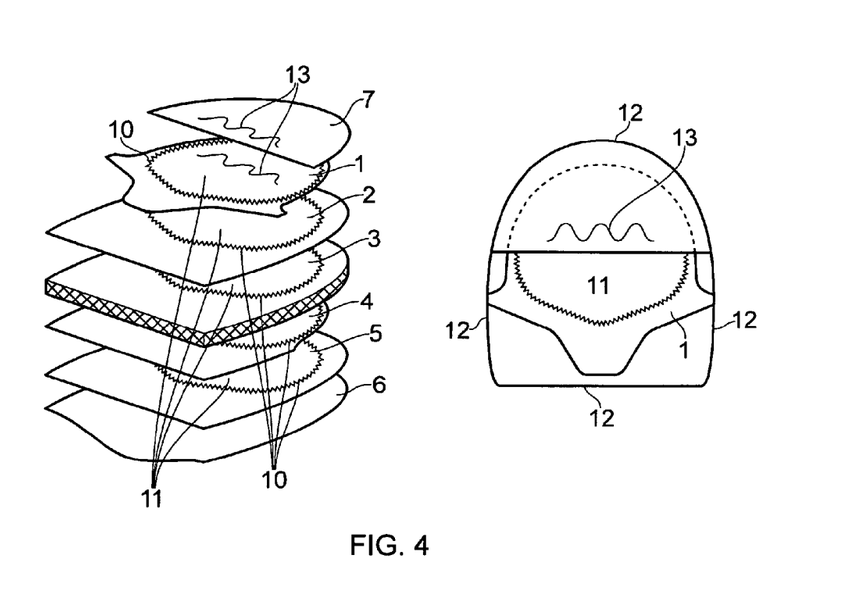
FIG. 4 shows another embodiment of a device according to the present invention, seen in an exploded view and from above.

Another embodiment of the present invention is shown in FIG. 4, where the construction of the pad is similar to the construction shown in FIG. 1. However, here the hinged layer 7 is connected to the top layer 1 through the weld or glue 13.

Figure 5:
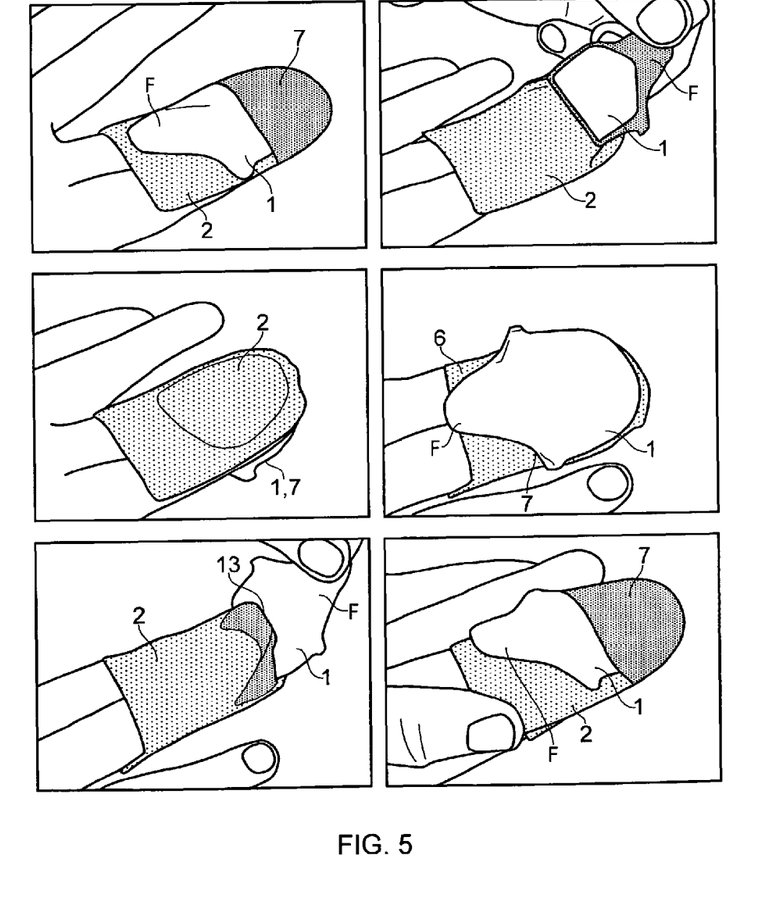
FIG. 5 shows the embodiment of the device illustrated in FIG. 4, where a hinged layer, connected to a top layer, is folded away to open the device.

When the laminated pad according to FIG. 4 is to be used, see also uppermost left figure in FIG. 5, either the hinged layer 7 or the top layer 1 can be used to unseal and prepare the laminated pad for use. As can be seen in the uppermost right figure, the top layer 1 is removed from the laminated pad by pulling off the flap F, whereby the user continues the movement in order to fold the top layer 1, and to the top layer 1 connected hinge layer 7, around the edge of the laminated pad. In the left middle figure this is shown, as the top layer 1 and the hinged layer 7 are folded around the edge of the laminated pad and are positioned on the opposite side of the contact layer 2. The right middle figure shows the laminated pad from the underside, where the top layer 1 and hinged layer 7 are removed and folded around the edge such that the top layer 1 and hinged layer 7 are brought into contact with the pocket layer 6. In the lowermost left figure the laminated pad has been used, whereby the top layer 1 and the hinged layer 7, being connected to each other by the weld or glue 13, are folded back to their initial position. This can be seen on the lowermost right figure, where the top layer 1 and the hinged layer 7 once again are arranged over the contact layer 2.

However, it should be understood that the unsealing of the laminated pad also can be provided by using the hinged layer 7 instead of the top layer 1.

Further modifications and alternative embodiments of the present invention will be apparent to those skilled in the art in view of this description. Accordingly, this description is to be construed as illustrative only and is for purpose of teaching those skilled in the art the manner of carrying out the invention. It is to be understood that the forms of the invention shown and described herewith, are to be taken as the presently preferred embodiment. Various changes may be made in the shape, size and arrangement of the different layers.

The invention claimed is:

1. A laminated pad for applying a quantity of a substance on a desired surface, wherein the laminated pad comprises an impermeable top layer and an impermeable trimmed bottom layer, between which two layers at least one layer is arranged, a utility layer further being arranged on an outside of the bottom layer, where the top layer, the at least one layer, the bottom layer and the utility layer through a weld are connected together to form a closed storage chamber for a substance that is to be contained in the laminated pad, wherein at least a part of the top layer and the bottom layer outside and around the closed storage chamber is cut off, in order to create a soft edge around the periphery of the laminated pad, where a hinged layer is arranged over the top layer, the hinged layer, the at least one layer and the utility layer being connected around their outer edges to form a laminated pad, such that the hinged layer can be turned inside out around the periphery of the laminated pad, the hinged layer further being connected to the top layer.

2. The laminated pad according to claim 1, wherein the hinged layer is manufactured from a soft and elastic material.

3. The laminated pad according to claim 1, wherein the hinged layer over a part of its outer periphery is connected to the other layers, thereby forming an opening between the hinged layer and the top layer.

4. The laminated pad according to claim 1, wherein the hinged layer only covers a part of the entire length of the laminated pad.

5. The laminated pad according to claim 1, wherein a pocket layer over a part of its outer periphery is connected to the other layers, the pocket layer together with the utility layer thereby forming an opening for a user's hand or finger(s).

6. The laminated pad according to claim 1, wherein the laminated pad further comprises a storage layer, where the storage layer consists of fibre structures in one or more planes, the fibre structures forming cavities containing the substance to be applied.

7. The laminated pad according to claim 1, wherein the laminated pad further comprises a contact layer, where the contact layer has a surface with a degree of roughness.

8. The laminated pad according to claim 7, wherein the contact layer comprises one or more layers with impermeable or partly impermeable films or laminates.

9. The laminated pad according to claim 1, wherein the top layer is provided with a flap.

\* \* \* \* \*